United States Patent [19]

Metcalf et al.

[11] 4,103,089
[45] Jul. 25, 1978

[54] α-ACETYLENE AND α-VINYL DERIVATIVES OF AMINO ACIDS

[75] Inventors: Brian Walter Metcalf, Strasbourg; Michel Jung, Illkirch Graffenstaden, both of France

[73] Assignee: Merrell Toraude et Compagnie, Strasbourg, France

[21] Appl. No.: 812,268

[22] Filed: Jul. 1, 1977

[51] Int. Cl.² .................................... C07D 233/64
[52] U.S. Cl. ............................ 548/344; 548/337; 544/28; 424/273 R
[58] Field of Search ............... 548/337, 342, 344

[56] References Cited

U.S. PATENT DOCUMENTS

| | | | |
|---|---|---|---|
| 3,169,971 | 2/1965 | Sletzinger et al. | 548/344 |
| 3,387,031 | 6/1968 | Johnson et al. | 548/344 |

*Primary Examiner*—Natalie Trousof
*Attorney, Agent, or Firm*—L. Ruth Hattan; Eugene O. Retter; George W. Rauchfuss, Jr.

[57] ABSTRACT

Novel acetylene and vinyl derivatives of amino acids of the following general structure

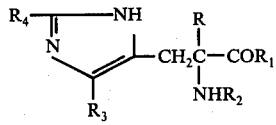

wherein R is —CH=CH₂ or C≡CH; R₁ is hydroxy, a straight or branched alkoxy group of from 1 to 8 carbon atoms, —NR₁₁R₁₂ wherein each of R₁₁ and R₁₂ is hydrogen or a straight or branched lower alkyl group of from 1 to 4 carbon atoms,

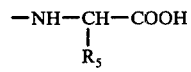

wherein R₅ is hydrogen, a straight or branched lower alkyl group of from 1 to 4 carbon atoms, benzyl or p-hydroxybenzyl; R₂ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

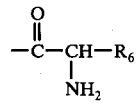

wherein R₆ is hydrogen, a straight or branched lower alkyl group of from 1 to 4 carbon atoms, benzyl or p-hydroxybenzyl; each of R₃ and R₄ is hydrogen, halogen selected from fluorine, chlorine, bromine and iodine, or a straight or branched lower alkyl of from 1 to 4 carbon atoms and may be the same or different with the proviso that when both R₃ and R₄ are halogen R₃ and R₄ are the same; with the proviso that when R is —CH=CH₂, R₁ is hydroxy and R₂ is hydrogen; and pharmaceutically acceptable salts thereof.

10 Claims, No Drawings

α-ACETYLENE AND α-VINYL DERIVATIVES OF AMINO ACIDS

FIELD OF INVENTION

This invention relates to novel pharmaceutically useful acetylenic derivatives of histidine and useful vinyl derivatives of histidine and related compounds.

BACKGROUND OF INVENTION

Most mammalian tissue contains histamine, concentration being particularly high in the skin, intestinal mucosa and the lungs. Every mammalian tissue that contains histamine, including white blood cells, appears capable of synthesizing the amine from histidine. The principal enzyme involved in catalyzing in vivo the conversion of histidine to histamine is histidine decarboxylase which is specific for the substrate L-histidine. In many tissues the chief storage site of histamine is the mast cell, or in the case of blood, the basophil which is the circulating counterpart of the fixed-tissue mast cell. Mast cells are not the only tissue source of histamine which is present in substantial amounts in the human epidermis, the central nervous system and the gastrointestinal mucosa.

Histamine is involved in various physiological processes. Histamine is released during the antigen-antibody reaction and is responsible, in large part, for the hypersensitivity reaction characterized by vasodilation, itching and edema formation. This type of antigen-antibody reaction wherein the principal cells involved are mast cells and basophils from which histamine is released is commonly referred to as an immediate hypersensitivity reaction. In addition to antigens, or allergens, histamine is released by many chemical substances, macromolecules, venoms, physical insult, such as heat and other injurious stimuli. Gastric acid secretion is known to be stimulated by histamine. Also, histamine is known to be frequently involved in initiation of sensory impulses evoking pain and itching. It has also been found that histamine levels are high in many tissues undergoing rapid growth, for example, embryonic tissue, regenerating liver and malignant growths.

Correlations between levels of histamine and histidine decarboxylase activity in tissues have been made. In the brain which contains histamine and histidine decarboxylase the turnover of histamine is rapid being augmented by stressful stimuli that also increases histidine decarboxylase activity. Inhibitors of L-histidine decarboxylase, such as, α-hydrazinohistidine are known to lower histamine concentrations. In rat fetal tissue, wherein high levels of histamine are present, it has been shown that inhibition of L-histidine decarboxylase arrests fetal development.

The effects of histamine and its mode of action are well documented. It is believed that the amine exerts its effect through at least two receptors being classified as $H_1$ and $H_2$ receptors. Several agents are known to counter the effects of histamine, however, not all such agents prevent the formation of histamine. For example, classical antihistamines useful in treating allergic reactions are believed to exert their utility by interfering with the binding of histamine with $H_1$ receptors. Similarly agents useful in countering the stimulant effect of histamine on gastric acid secretion are believed to operate by interfering with the binding of histamine with $H_2$ receptors.

Agents capable of blocking $H_1$ receptors find use in treating acute exudative types of allergy, such as, seasonal rhinitis, hay fever, pollinosis relieving the sneezing, rhinorrhea, itching eyes, nose and throat. Such agents are also useful in controlling cough and to a degree find use in treating systemic anaphylaxis and bronchial asthma. Antihistamine agents which act through $H_1$ receptors are also useful in treating allergic dermatoses, such as acute and chronic urticaria, angioedema, itching pruritides, for example, atopic dermatitis and contact dermatitis, in the control of urticarial and edematous lesions of serum sickness, control of blood transfusion reactions and control of drug reactions attributable to allergic phenomena. Agents which block $H_2$ receptors are useful in treating peptic ulceration, the Zollinger-Ellison syndrome and other gastric hypersecretory states.

Agents which block the formation of histamine by inhibiting the activity of histidine decarboxylase, for example, α-methylhistidine and α-hydrazinohistidine, are reported to be useful in the same manner as antihistaminic agents that are blockers of $H_1$ and $H_2$ receptors. Additionally histidine decarboxylase inhibitors are implicated as being useful in the control of certain tumors which are high in histamine content.

The compounds of the present invention wherein R is —C≡CH prevent the formation of histamine by inhibiting the action of histidine decarboxylase rendering said compounds useful in treating pathophysiological conditions which result from histamine. The presently claimed compounds can be used in the same manner and for the same purposes as are compounds that antagonize $H_1$ and $H_2$ receptors.

SUMMARY OF THE INVENTION

The compounds of the present invention are represented by the following general Formula I:

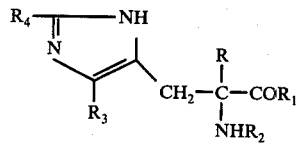

Formula I

In the above general Formula I R is —CH=$CH_2$ or —C≡CH; each of $R_3$ and $R_4$ is hydrogen, halogen selected from fluorine, chlorine, bromine and iodine or a straight or branched lower alkyl group of from 1 to 4 carbon atoms and can be the same or different with the proviso that when both $R_3$ and $R_4$ are halogen $R_3$ and $R_4$ are the same; $R_1$ is hydroxy, a straight or branched lower alkoxy group of from 1 to 8 carbon atoms, -$NR_{11}R_{12}$ wherein each of $R_{11}$ and $R_{12}$ is hydrogen or a straight or branched lower alkyl group of from 1 to 4 carbon atoms, or

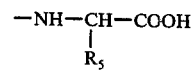

wherein $R_5$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

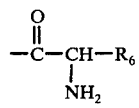

is hydrogen, a straight or branched lower alkyl group of from 1 to 4 carbon atoms, benzyl or p-hydroxybenzyl with the proviso that when R is —CH=CH$_2$, R$_1$ is hydroxy and R is hydrogen.

The pharmaceutically acceptable salts and individual optical isomers of the compounds of general Formula I are also included within the scope of this invention.

DETAILED DESCRIPTION OF INVENTION

Illustrative examples of straight or branched alkoxy groups of from 1 to 8 carbon atoms in the above general Formula I are methoxy, ethoxy, n-propoxy, n-butoxy, isopropoxy, tert-butoxy, pentoxy, and octyloxy.

Illustrative examples of straight chain or branched chain lower alkyl groups of from 1 to 4 carbon atoms in the above general Formula I are methyl, ethyl, n-propyl, isopropyl, n-butyl and tert-butyl.

As used in general Formula I the term alkylcarbonyl is taken to mean the group

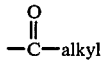

wherein the alkyl group is straight or branched and has from 1 to 4 carbon atoms, for example, methyl, ethyl, n-propyl, isopropyl, n-butyl and tert-butyl.

As used in general Formula I the term alkoxycarbonyl is taken to mean the group

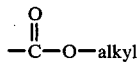

wherein the alkoxy group, that is, O-alkyl has from 1 to 4 carbon atoms and is straight or branched, for example, methoxy, ethoxy, n-propoxy, isopropoxy, n-butoxy and tert-butoxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, cyclamic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Preferred compounds of this invention are those of general Formula I wherein R is —C≡CH. Compounds wherein R is —C≡CH and R$_2$ is hydrogen or alkylcarbonyl wherein the alkyl moiety is straight or branched and has from 1 to 4 carbon atoms represent a more preferred embodiment of the invention. Compounds of general Formula I wherein R$_2$ is hydrogen or alkylcarbonyl as defined above, R$_1$ is hydroxy or a straight or branched alkoxy group of from 1 to 8 carbon atoms and R is —C≡CH are also preferred. The most preferred compounds of this invention are those of general Formula I wherein R is —C≡CH, R$_1$ is hydroxy or a straight or branched alkoxy group of from 1 to 8 carbon atoms, R$_2$ is hydrogen and each of R$_3$ and R$_4$ is hydrogen, chlorine, fluorine or methyl.

Illustrative examples of compounds of the present invention are the following:
2-acetylene-2-amino-3-(5-imidazolyl)propionic acid,
2-acetylene-2-amino-3-[5-(4-fluoro)imidazolyl]propionic acid,
2-acetylene-2-amino-3-[5-(2-fluoro)imidazolyl]propionic acid,
2-acetylene-2-amino-3-[5-(4-methyl)imidazolyl]propionic acid,
2-acetylene-2-amino-3-[5-(2-methyl)imidazolyl]propionic acid,
2-acetylene-2-amino-3-[5-(4-ethyl)imidazolyl]propionic acid,
2-acetylene-2-amino-3-[5-(2-ethyl)imidazolyl]propionic acid,
2-acetylene-2-amino-3-[5-(4-n-propyl)imidazolyl]propionic acid,
2-acetylene-2-amino-3-[5-(2-n-propyl)imidazolyl]propionic acid,
2-acetylene-2-amino-3-[5-(4-isopropyl)imidazolyl]propionic acid,
2-acetylene-2-amino-3-[5-(2-isopropyl)imidazolyl]propionic acid,
2-acetylene-2-amino-3-[5-(4-n-butyl)imidazolyl]propionic acid,
2-acetylene-2-amino-3-[5-(2-n-butyl)imidazolyl]propionic acid,
2-acetylene-2-amino-3-[5-(4-tert-butyl)imidazolyl]propionic acid,
2-acetylene-2-amino-3-[5-(2-tert-butyl)imidazolyl]propionic acid,
2-acetylene-2-amino-3-[5-(2,4-difluoro)imidazolyl]propionic acid,
2-acetylene-2-amino-3-[5-(2,4-dimethyl)imidazolyl]propionic acid,
2-acetylene-2-amino-3-[5-(2,4-diethyl)imidazolyl]propionic acid,
2-acetylene-2-amino-3-[5-(2,4-di-n-propyl)imidazolyl]propionic acid,
2-acetylene-2-amino-3-[5-(2,4-diisopropyl)imidazolyl]propionic acid,
2-acetylene-2-amino-3-[5-(2,4-di-n-butyl)imidazolyl]propionic acid,
2-acetylene-2-amino-3-[5-(2,4-di-tert-butyl)imidazolyl]propionic acid,
methyl 2-acetylene-2-amino-3-(5-imidazolyl)propionate,
ethyl 2-acetylene-2-amino-3-[5-(4-fluoro)imidazolyl]propionate,
n-propyl 2-acetylene-2-amino-3-[5-(2-fluoro)imidazolyl]propionate,
N-n-butyl 2-acetylene-2-amino-3-[5-(4-methyl)imidazolyl]propionamide,
isopropyl 2-acetylene-2-amino-3-[5-(2-methyl)imidazolyl]propionate,
tert-butyl 2-acetylene-2-amino-3-[5-(4-ethyl)imidazolyl]propionate,
n-pentyl 2-acetylene-2-amino-3-[5-(2-ethyl)imidazolyl]propionate,
isopentyl 2-acetylene-2-amino-3-[5-(4-n-propyl)imidazolyl]propionate, tert-pentyl 2-acetylene-2-amino-3-[5-(2-n-propyl)-imidazolyl]propionate,
n-hexyl 2-acetylene-2-amino-3-[5-(4-isopropyl-(imidazolyl]propionate, n-heptyl 2-acetylene-2-amino-3-[5-(2-isopropyl)imidazolyl]propionate,
n-octyl 2-acetylene-2-amino-3-[5-(4-n-butyl-)imidazolyl]propionate,
methyl 2-acetylene-2-amino-3-[5-(2-n-butyl)imidazolyl]propionate,
N,N'-dimethyl 2-acetylene-2-amino-3-[5-(4-tert-butyl)-imidazolyl]propionamide,
N-n-propyl 2-acetylene-2-amino-3-[5-(2,4-difluoro)-imidazolyl]propionamide,
N-n-butyl 2-acetylene-2-amino-3-[5-(2,4-dimethyl)-imidazolyl]propionamide,
ethyl 2-acetylene-2-amino-3-[5-(2,4-diethyl)imidazolyl]-propionate,
n-butyl 2-acetylene-2-amino-3-[5-(2,4-di-n-propyl)-imidazolyl]propionate,
N-ethyl 2-acetylene-2-amino-3-(5-imidazolyl)propionamide,
N-methyl 2-acetylene-2-amino-3-[5-(4-n-butyl-)imidazolyl]propionamide,
N-n-propyl 2 acetylene-2-amino-3-[5-(2-fluoro)imidazolyl]propionamide,
2-[2-acetylene-2-amino-3-(5-imidazolyl)-1-oxo-propylamino]acetic acid,
2-[2-acetylene-2-amino-3-[5-imidazolyl)-1-oxo-propylamino]propionic acid,
2-[2-acetylene-2-amino-3-[5-(2-methyl)imidazolyl]-1-oxopropylamino]-2-benzylacetic acid,
2-[2-acetylene-2-(1-oxoethylamino)-3-(5-(4-fluoro)-imidazolyl]-1-oxopropylamino)acetic acid,
2-[2-acetylene-2-(N-ethoxycarbonylamino)-3-[5-(4-methyl)imidazolyl]-1-oxopropylamino]acetic acid,
N,N'-diethyl 2-acetylene-2-(1-oxoethylamino)-3-[5-(2-fluoro)imidazolyl]propionamide,
2-acetylene-2-(1-oxoethylamino)-3-(5-imidazolyl)propionic acid,
2-acetylene-2-(N-propoxycarbonylamino)-3-[5-(2-methyl)-imidazolyl]propionic acid,
ethyl 2-acetylene-2-[N-(2-amino-1-oxoethyl)amino3-(5'-imidazolyl)propionate, and
N-methyl 2-acetylene-2-[N-(2-amino-1-oxo-3-phenyl-propyl)-amino]-3-[5'-(2-fluoro)imidazolyl]propionamide.
2-acetylene-2-amino-3-[5-(4-chloro)imidazolyl]propionic acid,
2-acetylene-2-amino-3-[5-(2-chloro)imidazolyl]propionic acid,
2-acetylene-2-amino-3-[5-(2-chloro-4-methyl-)imidazolyl]propionic acid,
2-acetylene-2-amino-3-[5-(2-bromo)imidazolyl]propionic acid,
2-acetylene-2-amino-3-[5-(2-iodo)imidazolyl]propionic acid,
2-amino-3-(5-imidazolyl)-2-vinylpropionic acid,
2-amino-3-[5-(4-fluoro)imidazolyl]-2-vinylpropionic acid,
2-amino-3-[5-(2-fluoro)imidazolyl]-2-vinylpropionic acid,
2-amino-3-[5-(2-methyl)imidazolyl]-2-vinylpropionic acid,
2-amino-3-[5-(2,4-dichloro)imidazolyl]-2-vinylpropionic acid,
2-amino-3-[5-(2,4-dimethyl)imidazolyl]2-vinylpropionic acid,
2-amino-3-[5-(2-ethyl-4-bromo)imidazolyl]-2-vinylpropionic acid,
2-amino-3-[5-(2,4-di-tert-butyl)imidazolyl]-2-vinylpropionic acid,
2-amino-3-[5-(4-iodo)imidazolyl]-2-vinylpropionic acid, and
2-amino-3-[5-(2-methyl-4-fluoro)imidazolyl]-2-vinylpropionic acid.

The compounds of Formula 1 wherein R is —C≡CH are irreversible inhibitors of histidine decarboxylase, the enzyme which in vivo converts histidine to histamine. Thus the compounds block the formation of histamine which is known to play an important role in certain patho-physiological conditions. As inhibitors of histidine decarboxylase the compounds of Formula I wherein R is —C≡CH are useful in the same manner as any known antihistiminic agent whether such agent exerts its effectiveness by blocking $H_1$ or $H_2$ receptors or other means. The compounds of Formula I wherein R is —C≡CH are useful in treating patho-physiological conditions due to histamine. Thus, the compounds have many utilities being useful in treating acute exudative types of allergy, such as, seasonal rhinitis, hay fever, and pollinosis relieving the sneezing, rhinorrhea, itching eyes, nose and throat. The compounds of general Formula I wherein R is —C≡CH are also useful in controlling cough and in treating systemic anaphylaxis and bronchial asthma, and are useful as bronchodilators. Also, the compounds of general Formula I wherein R —C≡CH are useful in treating allergic dermatoses, such as, acute urticaria, chronic urticaria, angioedema, itching pruritities, for example, atopic dermatitis and contact dermatitis. The compounds of general Formula I wherein R is —C≡CH are also useful in treating urticarial and edematous lesions of serum sickness, blood transfusion reactions attributable to allergic phenomena and nausea. The compounds of general Formula I wherein R is —C≡CH are also useful in treating peptic ulceration, the Zollinger-Ellison syndrome and other gastric hypersecretory states. As described hereinabove it has been found that histamine levels are high in rapidly growing tissues, such as, tumors, hence, the compounds of general Formula I wherein R is —C≡CH by inhibiting the formation of histamine, may be useful in controlling the growth of certain tumors, for example, Walker mammary carcinoma and Erlich ascitic tumors.

The compounds of Formula I wherein R is —C≡CH can be administered in various manners to achieve the desired effect. The compounds can be administered along or in the form of pharmaceutical preparations to the patient being treated either orally, parenterally, that is, subcutaneously, intravenously or intraperitoneally, or topically. The compounds can be administered by intranasal instillation or by application to mucous membranes such as that of the nose, throat and bronchial tubes, for example, in an aerosol spray containing small particles of a novel compound of this invention in a spray solution or dry powder form.

The amount of novel compound of Formula I wherein R is —C≡CH administered will vary and can be any effective amount. Depending on the patient, the condition being treated and the mode of administration, the quantity of novel compound administered may vary over a wide range to provide as an effective amount in a unit dosage form of from about 0.1 to 500 mg/kg (milligrams per kilogram) of body weight of the patient per dose and preferably from about 50 to 200 mg/kg to achieve the desired effect. For example, the desired effect can be obtained by consumption of a unit dosage form, such as, for example, a tablet containing from 10 to 500 mg of a novel compound of this invention taken 1 to 4 times daily.

As used herein the term patient is taken to mean warm blooded animals such as birds and mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of Formula I wherein R is —C≡CH and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents, such as corn starch, potato starch, or alginic acid, and a lubricant such as stearic acid, or magnesium stearate.

For parenteral administration the compounds of Formula I wherein R is —C≡CH may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds of Formula I wherein R is —C≡CH can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For use as aerosols the novel compounds of Formula I wherein R is —C≡CH in solution or suspension may be packaged in a pressurized aerosol container together with a gaseous or liquefied propellant, for example, dichlorodifluoromethane, dichlorodifluoromethane with dichlorodifluoroethane carbon dioxide, nitrogen or propane, with the usual adjuvants such as cosolvents, and wetting agents, as may be necessary or desirable. The compounds may also be administered in a nonpressurized form such as in a nebulizer or atomizer.

The utility of the compounds of general Formula I as irreversible inhibitors of histidine decarboxylase may be demonstrated as follows. A compound of general Formula I is administered as an aqueous solution or suspension to rats or mice either orally or parenterally. At different time intervals after administration of the test compound the animals are injected intraperitoneally with 2 μCi of 2-$^{14}$C-L-histidine. Two hours after the labeled histidine injection the animals are sacrificed, and the amount of radio active histamine present in the glandular part of the stomach is determined as described by K. M. Mole and D. M. Shepherd, J. Pharm. Pharmac. 25, 609-613 (1973).

In addition to being usful pharmacological agents, the compounds of Formula I wherein R is —C≡CH, $R_1$ is hydroxy and R is hydrogen are useful as intermediates for the preparation of cephalosporin derivatives of the following general Formula II which are useful as antibiotics.

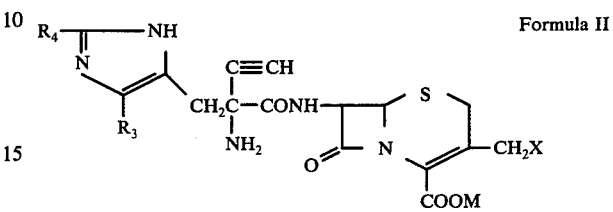

Formula II

In the above general Formula II X is hydrogen, acetoxy; M is hydrogen or a negative charge; and $R_3$ and $R_4$ have the meanings defined in general Formula I.

The compounds of general Formula II and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula II and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula II, salts and isomers thereof may be incorporated into creams or ointments.

Illustrative examples of bacteria against which the compounds of general Formula II and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula II are mineral acid addition salts, for example, hydrogen chloride, hydrogen bormide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of cephalosporin derivatives as represented by general Formula II are 7-[[2-acetylene-2-amino-3-(5-imidazolyl) propionyl]amino]-3-acetyloxymethyl-8-oxo-5-thia-1-azabicyclo[4.2.0]oct-2-ene-2-carboxylic acid, 7-[[2-acetylene-2-amino-3-[2-(methyl)-5-imidazolyl]propionyl]amino]-3-acetyloxymethyl-8-oxo-5-thia-1-azabicyclo[4.2.0]oct-2-ene-2-carboxylic acid and 7-[[2-acetylene-2-amino-3-[2-fluoro-5-imidazolyl]propionyl]amino]-3-acetyloxy-8-oxo-5-thia-1-azabicyclo[4.2.0]oct-2-ene-2-carboxylic acid.

The preparation of the compounds of general Formula II is described hereinbelow.

The compounds of general Formula I wherein R is —CH=CH₂ are useful as intermediates in the preparation of the compounds of general Formula I wherein R is —C≡CH which as indicated hereinabove are pharmacologically useful compounds.

The preparation of the compounds of general Formula I wherein R is —C≡CH, R₁ is hydroxy and R₂ is hydrogen are prepared by treating 1 equivalent of an appropriately substituted lower alkyl 2-amino-3-(5'-imidazolyl)-2-vinyl-propionate wherein the 1-imidazole nitrogen atom is protected with either a benzoyl or mono-trityl group and the α-amino group is protected with a benzoyl group in a chlorinated hydrocarbon solvent, such as, chloroform, methylene chloride or chlorobenzene or acetic acid with 1 equivalent of bromine at about 0° to 30° C with stirring for about 8 to 24 hours to give the corresponding nitrogen protected lower alkyl 2-amino-2-(1,2-dibromoethyl)-3-(5'-imidazolyl)propionate to which is added in an ether solvent, such as diethyl ether, tetrahydrofuran or dioxane or liquid ammonia a strong base after which the reaction mixture is stirred for from about 15 to 30 hours at about 0° to 25° C, quenched with water and the protected α-acetylene intermediate is heated for from 2 to 6 hours with hydrochloric acid to give the product as a salt which is isolated and purified by conventional means.

This reaction sequence is illustrated by the following:

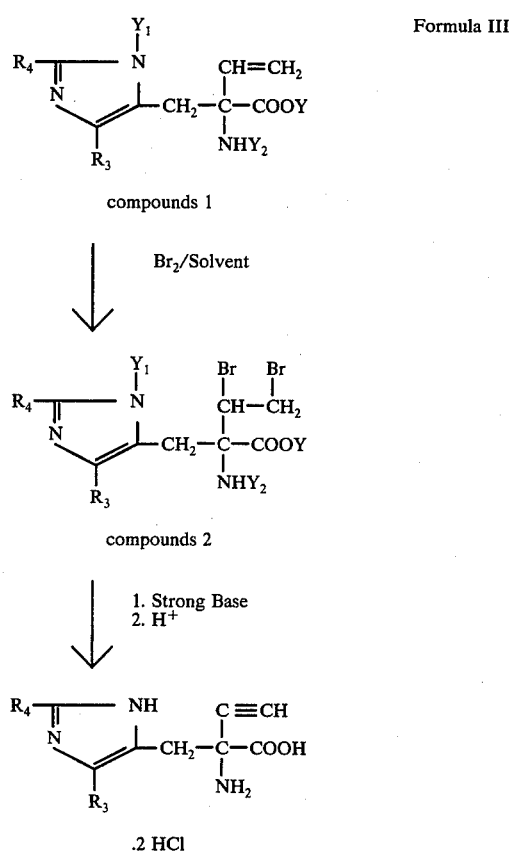

In the above reaction scheme R₃ and R₄ have the meanings defined in general Formula I, and Y represents a lower alkyl group, such as, methyl, ethyl or propyl; Y₁ is benzoyl or mono-trityl; and Y₂ is benzoyl, alkanoyl of from 1 to 4 carbon atoms or carbalkoxy wherein the alkoxy moiety has from 1 to 4 carbon atoms.

Suitable strong bases for the above described synthesis are alkyl lithium, for example, butyllithium, or phenyllithium, lithium di-alkylamide, for example, lithium diisopropylamide, lithium tetramethylpiperidide, lithium amide, tertiary potassium butylate, sodium amide or potassium amide. When in the above procedure liquid ammonia is employed as the solvent the base employed is lithium amide, potassium amide or sodium amide. The appropriately substituted lower alkyl N,N'-dibenzoyl-2-amino-3-(5'-imidazolyl)-2-vinylpropionate derivatives used in the above reaction, that is, compounds 1 are obtained by suspending an appropriately substituted α-vinyl histidine derivative, that is, a compound of the formula

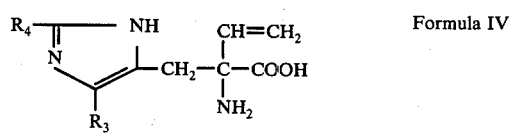

Formula IV in a lower alcohol, such as, methanol, ethanol or n-propanol saturated with anhydrous hydrochloric acid and stirring the suspension for from 8 to 24 hours at about 25° C to give α-vinylhistidine lower alkyl ester hydrochloride or chloroform and treated with benzoyl chloride and an organic amine such as triethylamine. The reaction mixture is stirred at about 25° C for from 6 to 30 hours and the α-acetylene-N,N'-dibenzoylhistidine methyl ester is isolated by conventional means.

The α-vinyl histidine derivatives, that is, compounds of general Formula IV wherein R₃ and R₄ have the meanings defined in general Formula I are prepared by treating an appropriately substituted N'-monotritylhistidine lower alkyl ester such as the methyl, ethyl or n-propyl ester in ether, such as, diethyl ether or tetrahydrofuran, aromatic hydrocarbons, such as, benzene, methylene chloride or chloroform with benzaldehyde, stirring the mixture for about 12 to 24 hours at about 0° to 25° C to form a Schiff's base. One equivalent of the Schiff's base in an ether solvent, such as, diethyl ether, dioxane or tetrahydrofuran or dimethylsulfoxide is added to one equivalent of a suitable strong base such as, alkyl lithium, for example, butyl lithium or phenyl lithium, lithium di-alkylamide, for example, lithium diisopropylamide, lithium amide, sodium hydride, tertiary potassium butylate or sodium amide, at a temperature of about −70° to 25° C followed 1 to 30 minutes later by addition of one equivalent of 2-chlorovinyl phenyl sulfone in an appropriate solvent, such as, ethers, for example, diethylether, dioxane or tetrahydrofuran or dimethylsulfoxide. The reaction mixture is allowed to warm to about 25° C and washed with, for example, aqueous ammonium chloride or sodium chloride and extracted, for example, with ether to give the appropriately substituted 3-carbalkoxy-3-benzylimino-4-(N-monotrityl-5-imidazolyl)but-1-enyl phenyl sulfone derivative which is treated with hydroxylamine, hydrazine or phenylhydrazine for about 5 minutes to 1 hour to give the corresponding free amine which is treated with 1 equivalent of an acid halide, such as acetyl chloride or benzoyl chloride or a lower alkyl haloformate, such as, methyl chloroformate and 1 equivalent or an organic amine, such as, a trialkylamine, illustratively triethylamine. The resulting carbamate or acylamide derivative is separated from benzaldehyde phenylhydrazone and treated with a suitable reducing agent, such as zinc in acetic acid, Raney nickel in a lower alcohol solvent, such as, methanol or ethanol or aluminum-mercury in ethers, such as, tetrahydrofuran, dimethoxyethane or dioxane or aqueous mixtures thereof for about 1 to 12 hours at reflux then washed with, for example, aqueous base, such as, aqueous sodium hydroxide, sodium carbonate or sodium bicarbonate followed by acid hydrolysis with, for example, 6 N hydrochloric acid for about 2 to 6 hours at reflux.

The appropriately substituted N'-monotritylhistidine lower alkyl esters are prepared from the corresponding ester hydrochlorides by treatment with a saturated solution of sodium bicarbonate, and the free base is extracted with chloroform. The tritylester hydrochlorides are prepared from histidine or histidine substituted at the 2 and/or 4-positions with a halogen selected from fluorine, chlorine, bromine or iodine or a lower alkyl group of from 1 to 4 carbon atoms and the 2- and 4- position substituents can be the same or different with the proviso that when both of the 2- and 4- position substituents are halogen they are the same by the general methods described by G. C. Stelakatos et al., J. Am. Chem. Soc. 81, 2884 (1959). The 2,4- substituted histidine derivatives are known in the art or can be prepared by procedures generally known in the art, for example, as illustrated in the specific examples contained herein.

The compounds of general Formula I wherein $R_1$ is a straight or branched alkoxy group of from 1 to 8 carbon atoms are prepared from the corresponding derivatives wherein $R_1$ is hydroxy by reaction with an alcohol of the formula $R_7$-OH, wherein $R_7$ is a straight or branched alkyl group of from 1 to 8 carbon atoms, such as, methyl, ethyl, n-propyl, isopropyl, n-butyl, tert-butyl, hexyl, or octyl, saturated with HCl gas at about 25° C for 12 to 36 hours.

The compounds of general Formula I wherein $R_1$ is $-NR_{11}R_{12}$ wherein each of $R_{11}$ and $R_{12}$ is hydrogen or a lower alkyl group of from 1 to 4 carbon atoms are prepared by an acylation reaction of an acid halide, for example, an acid chloride, of the corresponding compound wherein each $R_1$ is hydroxy and $R_2$ has the meaning defined in Formula I with the proviso that any free amino group is suitably protected with, for example, carbobenzyloxy or tert-butoxycarbonyl, and the 2-imidazole nitrogen is protected with carbobenzyloxy or 2,4-dinitrophenyl, with an excess of an appropriate amine which may be represented as $HNR_{11}R_{12}$. The reaction is carried out in methylene chloride, chloroform, dimethylformamide ethers, such as, tetrahydrofuran or dioxane, or benzene at about 25° C for about 1 to 4 hours. Suitable amines are ammonia, or a compound which is a potential source of ammonia, for example, hexamethylenetetramine; primary amines, for example, methylamine, ethylamine or n-propylamine; and secondary amines, for example, dimethylamine, diethylamine or di-n-butylamine. Following the acylation reaction the protecting groups are removed by treatment with acid, for example, trifluoroacetic acid or hydrogen bromide in dioxane followed by treatment with base such as aqueous sodium hydroxide.

The compounds of general Formula I wherein $R_1$ is

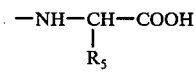

are prepared by reacting the corresponding derivative wherein $R_1$ is hydroxy or a functional derivative thereof such as an acid anhydride and $R_2$ has the meaning defined in Formula I with the proviso that any free amino group is protected with a suitable blocking group, such as benzyloxycarbonyl or tert-butoxycarbonyl and the 1-imidazole nitrogen is protected with benzyloxycarbonyl or 2,4-dinitrophenyl with a compound of the formula

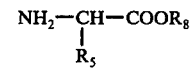

wherein $R_5$ has the meaning defined in general Formula I and $R_8$ is a lower alkyl group, for example, methyl or ethyl in an ether, for example, tetrahydrofuran or dioxane at 0° to 50° C for about 1 to 24 hours followed by acid and base hydrolysis to remove the protecting groups, with the proviso that when the amine protected free acid is employed the reaction is carried out using a dehydrating agent such as dicyclohexylcarbodiimide.

The compounds of general Formula I wherein $R_2$ is alkylcarbonyl wherein the alkyl moiety is straight or branched and has from 1 to 4 carbon atoms are prepared by treating the corresponding derivative wherein $R_1$ is hydroxy and $R_2$ is hydrogen with an acid halide of the formula

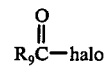

wherein halo is a halogen atom, for example, chlorine or bromine and $R_9$ is a straight or branched alkyl group having from 1 to 4 carbon atoms in water in the presence of a base such as sodium hydroxide or sodium borate at a temperature of from about 0° to 25° C for from about ½ hour to 6 hours. These compounds may also be prepared from the ester derivative, that is, compounds of general Formula I wherein $R_2$ is hydrogen and $R_1$ is an alkoxy group of from 1 to 8 carbon atoms by treatment with the acid halide,

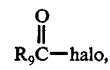

described above, in water, methylene chloride, chloroform or dimethyl acetamide in the presence of a base such as sodium hydroxide, potassium hydroxide or excess triethylamine at a temperature of from 0° to 25° C for from ½ hour to 24 hours.

The compounds of general Formula I wherein $R_2$ is alkoxycarbonyl wherein the alkoxy moiety is straight or branched and has from 1 to 4 carbon atoms are prepared by treating the corresponding derivative wherein $R_2$ is hydrogen and $R_1$ is hydroxy with a halo alkylformate of the formula

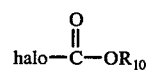

wherein halo is a halogen atom such as chlorine or bromine and $R_{10}$ is a straight or branched alkyl group having from 1 to 4 carbon atoms in water in the presence of a base such as sodium hydroxide or sodium borate at a temperature of from about 0° to 25° C for from about ½ hour to 6 hours.

The compounds of general Formula I wherein $R_2$ is

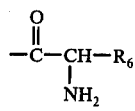

wherein $R_6$ is hydrogen, a straight or branched lower alkyl group of from 1 to 4 carbon atoms, benzyl or p-hydroxybenzyl are prepared by treating the corresponding derivative wherein $R_2$ is hydrogen, $R_1$ is a straight or branched alkoxy group of from 1 to 8 carbon atoms and the 1-imidazole nitrogen is protected with benzyloxycarbonyl or 2,4-dinitrophenyl with an acid of the formula

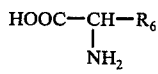

or an anhydride thereof wherein the amino group is protected with a suitable blocking group such as benzyloxycarbonyl or tert-butoxycarbonyl and $R_6$ has the meaning defined hereinabove in an ether, such as, tetrahydrofuran or dioxane, methylene chloride or chloroform, and in the presence of a dehydrating agent such as dicyclohexylcarbodiimide when the free acid is employed, at a temperature of from about 0° C to 35° C for about 1 to 12 hours followed by acid and base hydrolysis to remove the protecting groups.

Alternatively, the compounds of general Formula I wherein R is —C≡CH, $R_1$ is hydroxy and $R_2$ is hydrogen may be prepared by treating a suitably protected acetylenic amine of the Formula V

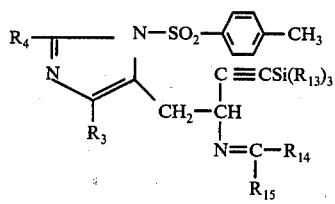

Formula V with a strong base to form a carbanion intermediate which is reacted with an acylating reagent and the protecting groups are subsequently removed by acid hydrolysis.

In the above Formula V, $R_3$ and $R_4$ have the meanings defined in general Formula I; $R_{14}$ is hydrogen, methoxy or ethoxy; and $R_{15}$ is phenyl, tert-butyl or triethylmethyl; and $R_{13}$ is a straight or branched lower alkyl group of from 1 to 4 carbon atoms, for example, methyl, ethyl, propyl or tert-butyl.

Suitable strong bases which may be employed in the above reaction to form each carbanion are those which will abstract a proton from the carbon atom ajacent to the acetylene moiety, such as, alkyl lithium, for example, butyl lithium or phenyl lithium, lithium di-alkylamide, for example, lithium diisopropylamide, lithium amide, tertiary potassium butylate or sodium amide.

Suitable acylating reagents which may be employed in the above reaction are halo-formates, such as chloro methylformate or chloro ethylformate, azido tert-butylformate, cyanogen bromide, carbon dioxide, diethylcarbonate, phenylisocyanate, triethoxymethylium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis with a lower alcohol, for example ethanol or isopropyl alcohol is required prior to deprotection by hydrolysis.

The acylating reaction may be carried out in an aprotic solvent, for example, benzene, toluene, ethers, tetrahydrofuran, dimethylsulfoxide, hexamethyl phosphortriamide. For each reaction the temperature varies from −120° C to about 25° C, a preferred reaction temperature being about −70° C, and the reaction time varies from about ½ hour to 24 hours.

Removal of the protecting groups is achieved by treatment with aqueous acid, for example, hydrochloric acid.

The compounds of Formula V wherein $R_{14}$ is hydrogen are prepared by the addition of protecting groups on the acetylene function and the nitrogen function of an appropriately substituted N-tosylimidazol-5-ylethylamine. Protection of the nitrogen function is accomplished by forming in a known manner a Schiff's base with a non-enolizable carbonyl bearing compound selected from benzaldehyde, 2,2-dimethylpropanal and 2,2-dimethylbutanal. Protection of the acetylenic function is accomplished by reacting the abovedescribed Schiff's base with a trialkylsilyl chloride wherein the alkyl moiety has from 1 to 4 carbon atoms and is straight or branched, for example, trimethylsilylchloride or triethylsilylchloride forming in a known manner the corresponding trialkylsilyl derivative.

The compounds of Formula V wherein $R_{14}$ is methoxy or ethoxy are prepared by reacting an appropriately substituted 1-acetylene-2-(1-toxylimidazol-5-yl)ethylamine wherein the acetylene function is protected by a trialkylsilyl group, wherein the alkyl moiety has from 1 to 4 carbon atoms and is straight or branched, with benzoyl chloride, pivalic acid chloride, or 2,2-diethylbutyric acid chloride at 0° C in diethyl ether, dioxane, tetrahydrofuran, chloroform, methylenechloride, dimethylformamide, dimethylacetamide, or chlorobenzene in the presence of an organic base such as triethylamine or pyridine after which the reaction mixture is allowed to warm to about 25° C for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_{14}$ is methoxy or triethyloxonium tetrafluoroborate when $R_{14}$ is ethoxy at about 25° C in a chlorinated hydrocarbon solvent such as methylene chloride, chlorobenzene or chloroform, and the reaction mixture is refluxed for about 12 to 20 hours. The mixture is then cooled to about 25° C and an organic base such as triethylamine or pyridine is added, after which the solution is extracted with brine and the product isolated.

The appropriately substituted 1-acetylene-2-(1-tosylimidazol-5-yl)ethylamine compounds used to obtain the protected acetylenic amine compounds of Formula V are prepared by reacting an appropriately substituted N-tosyl-5-imidazolylacetaldehyde of the Formula Formula VI

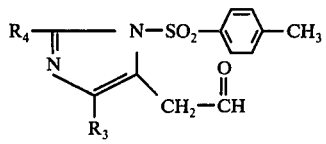

wherein R₃ and R₄ have the meanings defined in Formula I, with a metal acetylide of the formula HC≡CM' wherein M' is sodium, lithium or MgX' wherein X' is chlorine or bromine in a solvent such as liquid ammonia, dimethylsulfoxide or an ether, for example, tetrahydrofuran, dioxane, diethylether or dimethoxyethane at a temperature of about −78° C to 25° C for about 1 minute to 12 hours, preferably 1 hour to give the corresponding N-tosly-1-acetylene-2-imidazol-5-ylethanol. When sodium or lithium acetylide are employed liquid ammonia is the preferred solvent. When lithium acetylide is employed ether solvents are also preferred. Ether solvents are preferred when magnesium halide is employed with preferred reaction temperatures of about 0° to 25° C. When the complex lithium acetylide/ethylenediamine is employed the preferred solvent is dimethylsulfoxide with a temperature of 25° C and time of about 1 to 12 hours.

The N-tosyl-1-acetylene-2-imidazol-5-ylethanol is treated with phthalimide, triphenyl phosphine and diethyldiazodicarboxylate in ethers such as tetrahydrofuran, diethyl ether or dioxane for about 1 to 12 hours at about 25° to 50° C to afford the corresponding 1-phthalimido derivative which is treated with hydrazine hydrate in a lower alcohol solvent such as methanol or ethanol for about 1 to 6 hours at about 25° to 50° C. Alternatively the N-tosyl-1-acetylene-2-imidazol-5-ylethanol is treated with p-toluenesulfonyl chloride or mesyl chloride in a solvent such as an ether, for example, diethyl ether, dioxane or tetrahydrofuran, methylene chloride or chloroform in the presence of an organic amine such as pyridine or triethylamine, which may also serve as the solvent at a temperature of about 0° to 25° C for about 1 to 24 hours, preferably 12 hours; or with phosphorus trichloride in carbon tetrachloride, triphenylphosphine in carbon tetrachloride or carbon tetrabromide, or phosphorus tribromide, thionyl chloride or phosphorus pentachloride optionally in the presence of a solvent such as, an ether, for example, tetrahydrofuran, dioxane or diethyl ether, chloroform, methylene chloride, or benzene for about 1 to 24 hours at a temperature of about 0° to 80° C, preferably about 25° C followed by treatment with sodium amide and lithium amide in ammonia at about −78° C to −30° C for about 1 to 6 hours.

The compounds of general Formula VI are known in the art or can be prepared by procedures known in the art, for example, by treating an appropriately substituted histidine derivative with sodium hypochlorite in water at about 0° to 25° C for about 1 to 6 hours. The chloroamino acid without isolation is added to hot aqueous acid and undergoes decarboxylation to the aldehyde on standing from 1 to 24 hours at about 25° C or upon heating at about 30° to 100° C for about 1 to 3 hours. The thus obtained appropriately substituted imidazolyl acetaldehydes are treated in ethers such as tetrahydrofuran or diethyl ether, dichloromethane or chloroform with a base such as triethylamine or pyridine and p-toluenesulfonyl chloride at about 0° to 25° C for about 1 to 24 hours to afford the N-tosyl derivatives of Formula III.

The individual optical isomers of the compounds of Formula I wherein R₂ is H and R₁ is OH may be separated by using a (+) or (−) binaphthylphosphoric acid salt by the method of R. Viterbo et al., Tetrahedron Letters 48, 4617 (1971). The individual optical isomers of compounds wherein R₂ and R₁ are other than H and OH respectively are prepared as described herein for the racemic mixture only starting with the resolved amino acid.

As set forth hereinabove the compounds of general Formula I wherein R is —C≡CH, R₁ is hydroxy and R₂ is hydrogen are useful as intermediates for the preparation of useful cephalosporin derivatives as described by general Formula II. The compounds of general Formula II are prepared by coupling 7-aminocephalosporanic acid or a derivative thereof having the formula

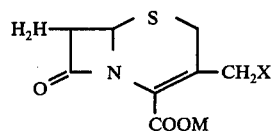

Formula V wherein X and M have the meaning defined in general Formula II with an acid of the following Formula VI or a functional derivative thereof, such as, the acid chloride or an acid anhydride

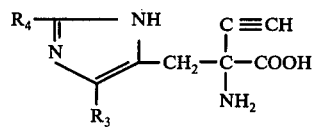

Formula VI wherein the amino groups are protected by suitable blocking groups, for example, an acid salt, such as hydrochloride salt, an acyl group, or tert-butoxycarbonyl which groups are removed after the coupling reaction by acid hydrolysis.

The coupling reaction is generally carried out in a solvent, such as, ethyl acetate, dioxane, chloroform or tetrahydrofuran in the presence of a base, such as alkaline bicarbonate. The temperature of the reaction may vary from −10° C to 100° C, and the reaction time may vary from about ½ hour to 10 hours. The cephalosporin products are isolated by conventional means.

EXAMPLE 1

2-Amino-3-(5-imidazolyl)-2-vinylpropionic acid

Methyl N'-monotrityl-2-amino-3-(5-imidazolyl)propionate hydrochloride (1.52 g, 0.034 M) is treated with a saturated solution of sodium bicarbonate, and the free base is extracted with chloroform. To a solution of the oily methyl N'-monotrityl-2-amino-3-(5-imidazolyl)propionate (1.31 g, .032 M) in 20 ml of methylene chloride is added 337 mg (.032 M) of benzaldehyde with stirring. Stirring is continued for 15 hours at about 25° C after which the mixture is concentrated to an oily residue which is crystallized in ether to give the Schiff's base methyl N'-monotrityl-2-benzylideneamino-3-(5-imidazolyl)-propionate, M.P. 132° C.

At −70° C 4.88 g (0.01 mole) of the Schiff's base in 30 ml of tetrahydrofuran is added to lithium diisopropylamide, prepared from 1.1 g (0.011 M) of diisopropylamine and 5.5 ml of a 2.0 M solution of n-butyllithium in 20 ml of tetrahydrofuran. After 20 minutes 2.02 g (0.01 M) of 2-chlorovinyl phenyl sulfone in 10 ml of tetrahydrofuran is added and the solution is allowed to warm to 25° C after which 50 ml of aqueous ammonium chloride is added, and the mixture is extracted with ether. The ether extract is concentrated to dryness, and the resulting residue dissolved in 50 ml of dichloromethane and treated with 1.08 g (0.01 mole) of phenyl hydrazine for one hour at 25° C. To this solution is added 1.01 g (0.01 mole) of triethylamine followed by 1.4 g (0.01 mole) of benzoyl chloride. The mixture is stirred for about 12 hours at 25° C then is washed with water (2 × 40 ml), dried over magnesium sulfate and applied to a column of silica (100 g). Elution with 2% methanol-chloroform afforded the benzamide as a yellow froth after evaporation of the solvent. The benzamide (4.0 g, 0.006 M) is dissolved in 500 ml of 10% aqueous tetrahydrofuran and treated with aluminum amalgam, prepared from 4.0 g aluminum and 2% aqueous mercuric chloride, for 4 hours at reflux. On cooling the suspension is filtered, the filtrate washed with ether and the organic solution washed with aqueous bicarbonate, dried and concentrated, leaving a residue. The residue is treated with 200 ml of 6 N HCl for 2 hours at reflux. After evaporation the residue is applied to an Amberlite resin 120 H+and eluting with 2 M ammonium hydroxide gives 2-amino-3-(5-imidazolyl)-2-vinylpropionic acid.

When in the procedure of Example 1 an appropriate amount of the hydrochloride of methyl N'-monotrityl-2-amino-3-[5-(2-fluoro)imidazolyl]propionate, methyl N'- monotrityl-2-amino-3-[5-(4-fluoro)imidazolyl]propionate, methyl N'-monotrityl-2-amino-3-[5-(2-methyl)imidazolyl]propionate, methyl N'-monotrityl-2-amino-3-[5-(4-methyl)imidazolyl]propionate, methyl N'-monotrityl-2-amino-3-[5-(2,4-difluoro)-imidazolyl]propionate, methyl N'-monotrityl-2-amino-3-[5-(2-fluoro-4-methyl)imidazolyl]propionate or methyl N'-monotrityl-2-amino-3-[5-(2,4-dichloro)imidazolyl]propionate is substituted for methyl N'-monotrityl-2-amino-3-[5-imidazolyl]propionate the following respective products are obtained:

2-amino-3-[5-(2-fluoro)imidazolyl]-2-vinylpropionic acid,
2-amino-3-[5-(4-fluoro)imidazolyl]-2-vinylpropionic acid,
2-amino-3-[5-(2-methyl)imidazolyl]-2-vinylpropionic acid,
2-amino-3-[5-(4-methyl)imidazolyl]-2-vinylpropionic acid,
2-amino-3-[5-(2,4-difluoro)imidazolyl]-2-vinylpropionic acid,
2-amino-3-[5-(2-fluoro-4-methyl)imidazolyl]-2-vinylpropionic acid, and
2-amino-3-[5-(2,4-dichloro)imidazolyl]-2-vinylpropionic acid.

The N-monotrityl derivatives employed to obtain the above listed vinyl derivatives are obtained from the appropriately substituted histidine derivative according to the general procedure described by G. C. Stelakatos et at., J. Am. Chem. Soc. 81, 2884 (1959).

EXAMPLE 2

Methyl N,N'-dibenzoyl-2-amino-3-(5-imidazolyl)-2-vinylpropionate

A suspension of 1.81 g (0.01 mole) of 2-amino-2-vinyl-3-(5-imidazolyl)propionic acid in 50 ml of methanol saturated with anhydrous HCl is stirred overnight at 25° C then evaporated to give 2-amino-2-vinyl-3-(5-imidazolyl)propionic acid methyl ester hydrochloride. The ester hydrochloride is suspended in 50 ml of methylene chloride and treated with 2.8 g (0.02 mole) of benzoyl chloride followed by treatment with 3.6 g (0.035 mole) of triethylamine. The mixture is stirred for 24 hours at 25° C, then washed with water, dried and evaporated. The residue is recrystallized from methanol to give methyl N,N'-dibenzoyl-2-amino-3-(5-imidazolyl)-2-vinylpropionate.

EXAMPLE 3

2-Acetylene-2-amino-3-(5'-imidazolyl)propionic acid dihydrochloride (A) A solution of 10g (0.02 m) of methyl N,N'-dibenzoyl-2-amino-3-(5-imidazolyl)-2-vinylpropionate in 200 ml of chloroform is treated with 3.2 g of bromine at 25° C. The mixture is stirred for 14 hours at 25° C after which the solvent is evaporated to afford crude N,N'-dibenzoyl-2-amino-2-(1,2-dibromoethyl)-3-(5-imidazolyl)propionic acid methyl ester.

(B) 13 g (0.02 M) of the crude dibromide in 50 ml of tetrahydrofuran is added at 0° C to lithium diisopropylamide, prepared from 5.7 g (0.057 M) of diisopropylamide and 28.5 ml of a 2.0 M solution of n-butyllithium. The solution is stirred for 24 hours at 0° C, quenched with water and extracted with ether. The ether extract is evaporated, and the resulting residue is heated with 100 ml of 6 N hydrochloric acid for three hours after which the aqueous solution is washed well with methylene chloride then evaporated. The residue is recrystallized from isopropyl alcohol to give 2-acetylene-2-amino-3-(5≡-imidazolyl)propionic acid hydrochloride.

When in the procedure of Example 2 an appropriate amount of 2-amino-3-[5-(2-fluoro)imidazolyl]-2-vinylpropionic acid, 2-amino-3-(5-(4-fluoro)imidazolyl)-2-vinylpropionic acid, 2-amino-3-[5-(2-methyl)imidazolyl]-2-vinylpropionic acid, 2-amino-3-[5-(4-methyl)imidazolyl]-2-vinylpropionic acid, 2-amino-3-[5-(2,4-difluoro)imidazolyl]-2-vinylpropionic acid, 2-amino-3-[5-(2-fluoro-4-methyl)imidazolyl]-2-vinylpropionic acid or 2-amino-3-[5-(2,4-dichloro)imidazolyl]-2-vinylpropionic acid is substituted for 2-amino-2-vinyl-3-(5-imidazolyl)propionic acid the following respective products are obtained:
methyl N,N'-dibenzoyl-2-amino-3-[5-(2-fluoro)imidazolyl]-2-vinylpropionate,
methyl N,N'-dibenzoyl-2-amino-3-[5-(4-fluoro)imidazolyl]-2-vinylpropionate,
methyl N,N'-dibenzoyl-2-amino-3-[5-(2-methyl)imidazolyl]-2-vinylpropionate,
methyl N,N'-dibenzoyl-2-amino-3-[5-(4-methyl)imidazolyl]-2-vinylpropionate,
methyl N,N'-dibenzoyl-2-amino-3-[5-(2,4-difluoro)imidazolyl]-2-vinylpropionate,
methyl-N,N'-dibenzoyl-2-amino-3-[5-(2-fluoro-4-methyl)-imidazolyl]-2-vinylpropionic acid, and
methyl N,N -dibenzoyl-2-amino-3-[5-(2,4-dichloro)imidazolyl]-2-vinylpropionic acid.

When in the procedure of Example 3(A) an appropriate amount of methyl N,N'-dibenzoyl-2-amino-3-[5-(2-fluoro)-imidazolyl]-2-vinylpropionate, methyl N,N'-dibenzoyl-2-amino-3-[5-(4-fluoro)imidazolyl]-2-vinylpropionate, methyl N,N'-dibenzoyl-2-amino-3-[5-(2-methyl)imidazolyl]-2-vinylpropionate, methyl N,N'-dibenzoyl-2-amino-3-[5-(4-methyl)-imidazolyl]-2-vinylpropionate, methyl N,N'-dibenzoyl-2-amino-3-[5-(2,4-difluoro)imidazolyl]-2-vinylpropionate, methyl N,N'-dibenzoyl-2-amino-3-[5-(2-fluoro-4-methyl)-imidazolyl]-2-vinylpropionic acid, or methyl N,N'-dibenzoyl-2-amino-3-[5-(2,4-dichloro)imidazolyl]-2-vinylpropionic acid is substituted for methyl N,N'-dibenzoyl-2-amino-3-(5-imidazolyl)-2-vinylpropionate and an appropriate amount of the respective crude dibromide derivatives thus obtained is used in the procedure of Example 3(B) the following respective products are obtained:

2-acetylene-2-amino-3-[5-(2-fluoro)imidazolyl]propionic acid dihydrochloride,
2-acetylene-2-amino-3-[5-(4-fluoro)imidazolyl]propionic acid dihydrochloride,
2-acetylene-2-amino-3-[5-(2-methyl)imidazolyl]propionic acid dihydrochloride, and
2-acetylene-2-amino-3-[5-(4-methyl)imidazolyl]propionic acid dihydrochloride,
2-acetylene-2-amino-3-[5-(2,4-difluoro)imidazolyl]propionic acid dihydrochloride,
2-acetylene-2-amino-3-[5-(2-fluoro-4-methyl-)imidazolyl]propionic acid dihydrochloride, and
2-acetylene-2-amino-3-[5-(2,4-dichloro)imidazolyl]propionic acid dihydrochloride.

The free bases of the compounds set forth above and in Example 3 can be obtained by treatment with a base by conventional means.

The following illustrates the use of the compounds of general Formula I wherein $R_1$ is hydroxy in the preparation of the useful cephalosporin derivatives of general Formula II.

EXAMPLE 4

7-[[2-Acetylene-2-amino-3-(5-imidazolyl)propionyl]amino]-3-acetoxymethyl-8-oxo-5-thia-1-azabicyclo[4.2.0]-oct-2-ene-2-carboxylic acid A mixture of 1 g of 3-acetyloxymethyl-7-amino-8-oxo-5-thia-1-azabicyclo[4.2.0]oct-2-ene-2-carboxylic acid and 1 g of 2-acetylene-2-amino-3-(5-imidazolyl)-propionic acid chloride wherein the free amino groups are protected with tertiary-butoxycarbonyl in 50 ml of ethyl acetate is refluxed for 2 hours after which the solvent is removed leaving a residue which is chromatographed on silica gel using benzene-acetone as the eluant to give 7-[[2-acetyl-ene-2-amino-3-(5-imidazolyl)-propionyl]amino]-3-acetoxymethyl-8-oxo-5-thia-1-azabicyclo[4.2.0]oct-2-ene-2-carboxylic acid wherein the amino groups are protected with tert-butoxycarbonyl. The protected cephalosporin compound is treated with trifluoroacetic acid for ½ hour at 25° C under nitrogen atmosphere then diluted with ether until precipitation stops and filtered to give the di-tri-fluoroacetic acid salt of the title cephalosporin which can be converted to free base by use of ion exchange resin.

The following examples are illustrative of pharmaceutical preparations of compounds of general Formula I wherein R is —C≡CH.

EXAMPLE 5

An illustrative composition for hard gelatin capsules is as follows:

| (a) | 2-acetylene-2-amino-3-(5-imidazolyl)-propionic acid | 100 mg |
|---|---|---|
| (b) | talc | 20 mg |
| (c) | lactose | 500 mg |

The formulation is prepared by passing the dry powders of (a) and (b) through a fine mesh screen and mixing them well. The powder is then filled into hard gelatin capsules at a net fill of 620 mg per capsule.

EXAMPLE 6

An illustrative composition for tablets is as follows:

| (a) | 2-acetylene-2-amino-3-(5-imidazolyl)propionic acid | 200 mg |
|---|---|---|
| (b) | starch | 50 mg |
| (c) | lactose | 100 mg |
| (d) | magnesium stearate | 5 mg |

The granulation obtained upon mixing the lactose with the compound (a) and part of the starch and granulated with starch paste is dried, screened, and mixed with the magnesium stearate. The mixture is compressed into tablets weighing 355 mg each.

EXAMPLE 7

An illustrative composition for an aerosol solution is the following:

| | | Weight per cent |
|---|---|---|
| (a) | 2-acetylene-2-amino-3-[5-(2-fluoro)imidazolyl)propionic acid | 20.0 |
| (b) | ethanol | 30.0 |
| (c) | dichlorodifluoromethane | 50.0 |

The materials (a), (b) and (c) are packaged in 15 ml stainless steel containers equipped with a metering valve designed to meter 0.2 grams per dose, an equivalent of 40 mg of novel compound (a).

EXAMPLE 8

An illustrative composition for an injectable suspension is the following 1 ml ampul for an intramuscular injection.

| | | Weight per cent |
|---|---|---|
| (a) | 2-acetylene-2-amino-3-[5-(4-methyl)imidazolyl]propionic acid | 5.0 |
| (b) | polyvinylpyrrolidone (M.W. 25000) | 0.5 |
| (c) | lecithin | 0.25 |
| (d) | water for injection to make | 100.0 |

The materials (a) – (d) are mixed, homogenized, and filled into 1 ml ampuls which are sealed and autoclaved 20 minutes at 121° C. Each ampul contains 50 mg per ml of novel compound (a).

EXAMPLE 9

An illustrative composition for an aerosol suspension is the following:

| | | Weight per cent |
|---|---|---|
| (a) | 2-acetylene-2-amino-3-[5'-imidazolyl)propionic acid (particle size <10 μ) | 20.0 |
| (b) | sorbitan trioleate | 0.5 |
| (c) | dichlorodifluoromethane | 39.75 |
| (d) | dichlorodifluoroethane | 39.75 |

The materials (a) – (d) are packaged in 15 ml stainless steel containers equipped with a metering valve designed to meter 50 mg per dose, an equivalent of 10 mg of novel compound (a).

EXAMPLE 10

N-Acetyl-2-acetylene-2-amino-3-(5-imidazolyl)propionic acid

A solution of 1.8 g (0.01 mole) of 2-acetylene-2-amino-3-(5-imidazolyl)propionic acid in 12 ml of 2 N sodium hydroxide solution is cooled to 5° C. To this solution, maintained at 5° C, are added simultaneously from two syringes 1.0 g (0.013 mole) of acetyl chloride and 26 ml 2N sodium hydroxide dropwise. After 2 hours the solution is neutralized by the addition of 8 ml of 5 N hydrochloric acid followed by 0.5 ml of acetic acid. The mixture is cooled to 0° C and the resultant N-acetyl-2-acetylene-2-amino-3-(5-imidazolyl)propionic acid filtered off.

EXAMPLE 11

Methyl-2-acetylene-2-amino-3-(5-imidazolyl)propionate, dihydrochloride

A suspension of 4.4 g (0.024 mole) of 2-acetylene-2-amino-3-(5-imidazolyl)propionic acid in 30 ml of methanol at 0° C is saturated with dry hydrogen chloride after which the solution is heated under reflux for 12 hours. The solution is then concentrated and allowed to crystallize to afford methyl-2-acetylene-2-amino-3-(5-imidazolyl)propionate, dihydrochloride (4.0 g).

EXAMPLE 12

Ethyl-N-acetyl-2-acetylene-2-amino-3-(5-imidazolyl)propionate monohydrochloride

A solution of 2.0 g (0.009 mole) of N-acetyl-2-acetylene-2-amino-3-(5-imidazolyl)propionic acid in 50 ml of ethanol is saturated with dry hydrogen chloride, then heated under reflux overnight. The solution is concentrated then cooled and the ethyl ester monohydrochloride filtered off.

EXAMPLE 13

2-Acetylene-2(2-aminopropionamido)-3-(5-imidazolyl)propionic acid

A solution of 1.9 g (0.01 mole) of methyl 2-acetylene-1-amino-3-(5-imidazolyl)propionate and 2.1 g (0.02 mole) of triethylamine in 40 ml of dichloromethylene at 25° C is treated with 3.4 g (0.02 mole) of benzyl chloroformate. After 2 hours at 25° C the solution is washed with water, dried and concentrated to afford the dicarbobenzoxy methyl ester. To this residue is added 30 ml of 40% (w/w) hydrogen bromide in dioxane and the mixture allowed to stand at 25° C for 30 minutes. Ether (150 ml) is then added and the resultant precipitate is filtered off and added to cold bicarbonate solution then rapidly extracted into dichloromethane. The dichloromethane solution is dried and concentrated to afford methyl N-carbobenzoxy-2-acetylene-2-amino-3-(5-imidazolyl)propionate (2.3 g, 0.007 mole) which is treated in 10 ml of dichloromethane with 1.6 g (0.007 mole) of N-carbobenzoxy alanine and 1.45 g (0.007 mole) of N,N'-dicyclohexylcarbodimide overnight at 25° C. The mixture is then cooled to 0° C, the precipitated dicyclohexyl urea filtered off, the organic solution washed with 1 N hydrochloric acid, bicarbonate solution, then dried and concentrated. The residue is then treated with 30 ml of 40% (w/w) hydrogen bromide in dioxane for 30 minutes at 25° C. Addition of 150 ml of ether resulted in a precipitate of the hydrobromide which was filtered off and treated overnight with 50 ml of 1 N sodium hydroxide at 25° C. The resulting solution is adjusted to neutral pH and the product isolated from an Amberlite 120 H$^+$resin by elution with ammonia (1 M).

EXAMPLE 14

N-(2-Propionic acid)-2-acetylene-2-amino-3-(5-imidazolyl)propionyl carboxamide

To a solution of 1.8 g (0.01 mole) of 2-acetylene-2-amino-3-(5-imidazolyl)propionic acid in 5 ml of 4 N sodium hydroxide is added 10 ml of 5% sodium carbonate and 8 ml of dioxane. The solution is cooled in an ice bath and treated with 3.9 g (0.021 mole) of benzyl chloroformate and 5 ml of 4 N sodium hydroxide, added dropwise and simultaneously from two dropping funnels. The mixture is stirred for an additional 20 minutes at 0° C, then 30 ml of ethyl acetate is added and the reaction mixture is neutralized with 6 N hydrochloric acid. The aqueous phase is extracted with ethyl acetate, the organic solutions combined, dried and concentrated to about 5 ml. Ether (15 ml) is added and the N,N'-dicarbobenzoxy-2-acetylene-2-amino-3-(5-imidazolyl)-propionic acid (2.9 g, 0.007 mole) filtered off. The N,N'-dicarbobenzoxy derivative is dissolved in 15 ml of methylene chloride and treated with 720 mg (0.007 mole) of alanine methyl ester in 5 ml of methylene chloride and 1.45 g (0.007 mole) of N,N'-dicyclohexylcarbodimide. The mixture is allowed to stand overnight at 25° C, then refrigerated and the precipitated dicyclohexyl urea filtered off. The filtrate is washed with N hydrochloric acid followed by 5% bicarbonate, then dried and concentrated to afford N-(2-propionic acid methyl ester)-N,N'-dicarbobenzoxy-2-acetylene-2-amino-3-(5-imidazolyl)-propionyl carboxamide which is dissolved in dioxane containing 15 ml of 40% (w/w) hydrogen bromide and allowed to stand at room temperature for 30 minutes. Ether (100 ml) is added and the resulting precipitate collected and suspended in 50 ml of 0.8 N NaOH and stirred overnight at 25° C. The aqueous solution is extracted with ether, neutralized, and applied to an Amberlite 120 H$^+$ resin and the product isolated by elution with ammonia (1 M).

EXAMPLE 15

N-(n-Propyl)-2-acetylene-2-amino-3-(5-imidazolyl)propionyl carboxamide, dihydrochloride N,N'-Dicarbobenzoxy-2-acetylene-2-amino-3-(5-imidazolyl)propionic acid (2.9 g, 0.007 mole), prepared as described for N-(2-propionic acid)-2-acetylene-2-amino-3-(5-imidazolyl)propionyl carboxamide, in 30 ml of dichloromethane is treated with 82.5 mg (0.007 mole) of thionyl chloride at 25° C for one hour. Propylamine (820 mg, 0.014 mole) is added and the solution stirred at 25° C for another hour. The solution is then washed with water, dried and evaporated. The residue is treated with 15 ml of a solution of dioxane containing hydrogen bromide (40% w/w) and ethanol and allowed to stand for 30 minutes at 25° C. Ether (50 ml) is then added, the resulting precipitate collected and treated with 200 ml of 1 N sodium hydroxide and 20 ml of methanol overnight at 25° C. The solvents are concentrated by evaporation and the solution extracted with dichloromethane.

The organic phase is in turn extracted with 1 N HCl and the aqueous phase evaporated to afford the product.

EXAMPLE 16

2-Fluoro-4-methylhistidine

4-Methylhistidine methyl ester (free base) (10 g) is added to 35 ml of trifluoroacetic anhydride at −10° C. The mixture is stirred at 25° C for 5 hours, then the solvent is removed under reduced pressure. Water (50 ml) is added then removed in vacuo, this procedure being repeated 3 times, followed by similar treatment with ethanol. The residue is recrystallized from ethyl acetate-ether to afford α-N-trifluoroacetyl-4-methylhistidine methyl ester as the trifluoracetate salt.

A solution of 1.44 g (200 mM) of NaNO$_2$ in 20 ml of water at 0° C is added to a solution of 2.44 g (0.02 mole) of p-bromoaniline in 300 ml of 2.3 N HCl at 0° C. After 40 minutes at 0° C the resulting solution of the diazonium salt is added to a solution of α-N-trifluoroacetyl-4-methyl histidine methyl ester (5.5 g, 0.1 M, from the trifluoroacetate salt) in 200 ml of 0.2 M aqueous sodium carbonate. After 2 hours at 0° C the orange precipitate (6.0 g) is collected and dried, then suspended in 200 ml of ethanol containing 0.5 g of platinum oxide and subjected to catalytic hydrogen (25° C, 40 psi Paar bomb) overnight after which the catalyst is filtered off and the solvent evaporated. The residue is treated with 100 ml of water, filtered and washed with ether. The aqueous layer is evaporated and the residue recrystallized from ethanolether to afford α-N-trifluoroacetyl-2-amino-4-methylhistidine methyl ester.

To 100 ml of 50% aqueous HBF$_4$ at −10° C is added α- N-trifluoroacetyl-2-amino-4-methylhistidine methyl ester (2.5 g, 8.6 mM), followed by NaNO$_2$ (0.8 g, 12 mM) in 5 ml of water. This solution is diluted with 100 ml of cold HBF$_4$ and irradiated at 0° C with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethylacetate. The ethyl acetate solution is concentrated to afford an oily residue which is treated with 15 ml of 0.5 M sodium hydroxide for 4 hours at 25° C. After neutralization the solution is applied to an Amberlite 120 H$^+$ resin, and the product eluted with NH$_4$OH (1 M). Evaportion of the ammonia and recrystallization from methanol gives 2-fluoro-4-methylhistidine.

EXAMPLE 17

4-Fluoro-2-methylhistidine

2-Methylhistidine methyl ester (free base) (10 g) is added to 35 ml of trifluoroacetic anhydride at −10° C. The mixture is stirred at 25° C for 5 hours, then the solvent is removed under reduced pressure. Water (50 ml) is added and then removed in vacuo, this procedure being repeated 3 times, followed by a similar treatment with ethanol. The residue is recrystallized from ethyl acetate-ether to afford α-N-trifluoroacetyl-2-methylhistidine methyl ester as its trifluoroacetate salt.

A solution of 1.44 g (200 mM) of NaNO$_2$ in 20 ml of water at 0° C is added to a solution of 3.44 g (0.02 mole) of p-bromoaniline in 100 ml of 2.3 N HCl at 0° C. After 40 minutes at 0° C the resulting solution of the diazonium salt is added to a solution of α-N-trifluoroacetyl-4-methyl histidine methyl ester (5.5 g, 0.1 M, from the trifluoroacetate salt) in 200 ml of 0.2 M aqueous sodium carbonate. After 2 hours at 0° C the orange precipitate (6.0 g) is collected and dried, then suspended in 200 ml of ethanol containing 0.5 g platinum oxide and subjected to catalytic hydrogen (25° C, 40 psi Paar bomb) overnight. The catalyst is filtered off and the solvent evaporated. The residue is treated with 100 ml of water, filtered and washed with ether. The aqueous layer is evaporated and the residue recrystallized from ethanol-ether to afford α-N-trifluoroacetyl-2-methyl-4-aminohistidine methyl ester.

To 100 ml of 50% aqueous HBF$_4$ at −10° C is added α-N-trifluoroacetyl-2-methyl-4-aminohistidine methyl ester (2.5 g, 8.6 mM) followed by NaNO$_2$ (0.8 g, 12 mM) in 5 ml of water. This solution is diluted with cold HBF$_4$ (100 ml) and irradiated at 0° C with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethyl acetate. The ethyl acetate solution is concentrated to afford an oily residue which is treated with 15 ml of 0.5 M sodium hydroxide for 4 hours at 25° C. After neutralization the solution is applied to an Amberlite 120 H$^+$ resin, and the product eluted with NH$_4$OH (1M). Evaporation of the ammonia and recrystallization from methanol gives 4-fluoro-2-methylhistidine.

EXAMPLE 18

2,4-Difluorohistidine

A solution of 1.44 g (200 mM) of NaNO$_2$ in water (20 ml) at 0° C is added to a solution of p-bromoaniline (6.88 g, 0.04 M) in HCl (200 ml of 2.3 N) at 0° C. After 40 minutes at 0° C the resulting solution of the diazonium salt is added to a solution of α-N-benzoylhistidine methyl ester (5.5 g, 0.1 M) in aqueous Na$_2$CO$_3$ (400 ml of 0.2 M). After 2 hours at 0° C the orange precipitate (12.0 g) is collected and dried, then suspended in 400 ml of ethanol containing 0.5 g of platinum oxide and subjected to catalytic hydrogen (25° C, 40 psi Paar bomb) overnight. The catalyst is filtered off and the solvent evaporated. The residue is treated with 200 ml of water, filtered and washed with ether. The aqueous layer is evaporated and the residue recrystallized from ethanol-ether to afford α-N-benzoyl-2,4-diaminohistidine methyl ester.

To 100 ml of 50% aqueous HBF$_4$ at −10° C is added α-N-benzoyl-2,4-diamino histidine methyl ester (2.5 g), followed by NaNO$_2$ (1.6 g, 24 mM) in water (10 ml). This solution is diluted with cold HBF$_4$ (200 ml) and irradiated at 0° C with a Hanovia 450-W medium-pressure mercury vapor lamp, equipped with a Corex filter, in a quartz immersion well. After 1 hour irradiation time the reaction mixture is neutralized to pH 6 with cold concentrated sodium hydroxide, then extracted with ethyl acetate. The ethyl acetate solution is concentrated to afford an oily residue which is treated with NaOH (0.5 M, 30 ml) for 14 hours at 25° C. After neutralization the solution is applied to an Amberlite 120 H$^+$ resin, and the product eluted with NH$_4$OH (1 M). Evaporation of the ammonia and recrystallization from methanol gives 2,4-difluorohistidine.

The 2-alkyl or 4-alkyl and the 2,4-dialkylhistidine derivatives employed herein are prepared from 5-hydroxymethylimidazole substituted at the 2 and/or 4-positions with an appropriate lower alkyl group by the general procedure described by K. Matsumoto et al., Agr. Biol. Chem. 38 (5), 1097 (1974). The 2,4-dialkyl-5-hydroxymethylimidazoles are prepared by hydroxymethylation of the 2,4-dialkylimidazole with formaldehyde by the general procedure of M. Masui et al., Chem. Pharm. Bull. 1974, 2359. The 4-alkyl-5-hydroxymethylimidazoles are similarly prepared according to the method described by Ewins, J. Chem. Soc. 99, 2052 (1911). The 2-alkyl-5-hydroxymethylimidazoles are prepared by hydroxymethylation of 1-benzyl-2-alkylimidazoles to give 1-benzyl-2-alkyl-4-hydroxymethylimidazoles according to E. F. Godefroi et al., Rec. Trav. Chim. Pays Bas 91, 1385 (1972). The N-benzyl group is subsequently removed using Na/NH₃ as described, for example, by R. G. Jones, J. Am. Chem. Soc. 71, 383 (1949).

EXAMPLE 19

2,4-Dichlorohistidine

To a solution of 1.6 g (24 mM) of sodium nitrite in 16 ml of concentrated sulfuric acid at 25° C is added 2.5 g (8.6 mM) of α-N-benzoyl-2,4-diaminohistidine in 20 ml of acetic acid at such a rate as to maintain the temperature below 35° C. This solution is then added with cooling to a solution of 10 g of cuprous chloride in 20 ml of concentrated hydrochloric acid. The combined solution is maintained at 25° C for 10 minutes then neutralized by careful addition of cold concentrated sodium hydroxide followed by extraction with ethyl acetate. The ethyl acetate extract is concentrated to afford an oily residue which is treated with 30 ml of 0.5 M sodium hydroxide for 14 hours at 25° C. After neutralization the solution is applied to an Amberlite 120 H⁺ resin and eluting with 1 M ammonium hydroxide and evaporation of the ammonia affords 2,4-dichlorohistidine upon recrystallization from methanol.

When in the above procedure of Example 19 an appropriate amount of cuprous bromide is substituted for cuprous chloride and hydrobromic acid is used in place of hydrochloric acid, 2,4-dibromohistidine is obtained.

The 2,4-diiodohistidine compound [D. Mackay and D. M. Shepherd, Brit. J. Pharmacol. 15, 552 (1960)] is obtained from the diazonium salt formed in situ in the procedure of Example 19, by pouring said salt into aqueous potassium iodide containing aqueous iodide.

When in the above procedure of Example 19 an appropriate amount of the α-N-benzoyl derivative of 2-amino-4-(lower)alkylhistidine methyl ester, 2-(lower)alkyl-4-aminohistidine methyl ester, wherein the lower alkyl group has from 1 to 4 carbon atoms and is straight or branched, 2-aminohistidine or 4-aminohistidine is substituted for α-N-benzoyl-2,4-diaminohistidine the following compounds are obtained:
2-chloro-4-(lower)alkylhistidine,
2-(lower)alkyl-4-chlorohistidine,
2-chlorohistidine and
4-chlorohistidine,
and when the procedure of Example 19 is further modified by substituting an appropriate amount of cuprous bromide for cuprous chloride and hydrobromic acid is substituted for hydrochloric acid the following compounds are obtained: 2-bromo-4-(lower)alkylhistidine, 2-(lower)alkyl-4-bromohistidine, 2-bromohistidine and 4-bromohistidine.

The 2- or 4-diodohistidine derivatives and the 2-iodo-2-(lower)alkyl histidine derivatives are obtained from the 2- or 4-diazoniumhistidine derivative and the 2-diazonium-4-(lower)alkylhistidine derivatives by pouring the appropriate diazonium derivative into aqueous potassium iodide containing aqueous iodide. The 2- or 4-diazoniumhistidine derivative and the 2-diazonium-2-(lower)alkylhistidine derivatives are formed in situ when in the procedure of Example 19 the α-N-benzoyl derivative of 2- or 4-aminohistidine, 2-amino-4-(lower)alkylhistidine or 4-amino-2-(lower)alkylhistidine is substituted respectively for α-N-benzoyl-2,4-diaminohistidine.

We claim:

1. A compound of the formula

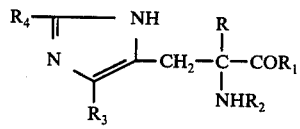

wherein R is —CH=CH₂ or —CH≡CH; each of R₃ and R₄ is hydrogen, halogen selected from fluorine, chlorine, bromine and iodine or a straight or branched lower alkyl group of from 1 to 4 carbon atoms and can be the same or different with the proviso that when both R₃ and R₄ are halogen R₃ and R₄ are the same; R₁ is hydroxy, a straight or branched alkoxy group of from 1 to 8 carbon atoms, —NR₁₁R₁₂ wherein each of R₁₁ and R₁₂ is hydrogen or a straight or branched lower alkyl group of from 1 to 4 carbon atoms or

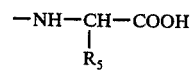

wherein R₅ is hydrogen, a straight or branched lower alkyl group of from 1 to 4 carbon atoms, benzyl or p-hydroxybenzyl; R₂ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

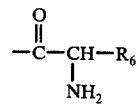

wherein R₆ is hydrogen, a straight or branched lower alkyl group of from 1 to 4 carbon atoms, benzyl or p-hydroxybenzyl; with the proviso that when R is —CH=CH₂, R₁ is hydroxy and R is hydrogen; and pharmaceutically acceptable salts and individual optical isomers thereof.

2. A compound of claim 1 wherein R is —CH=CH₂.

3. A compound of claim 2 wherein each of R₃ and R₄ is hydrogen, chlorine, fluorine or methyl.

4. A compound of claim 1 wherein R is —C≡CH.

5. A compound of claim 4 wherein R₂ is hydrogen or alkylcarbonyl.

6. A compound of claim 4 wherein R₁ is hydroxy or a straight or branched alkoxy group of from 1 to 8 carbon atoms.

7. A compound of claim 4 wherein each of R₃ and R₄ is hydrogen, chlorine, fluorine or methyl.

8. A compound of claim 1 wherein R is —C≡CH, R₁ is hydroxy or a straight or branched alkoxy group of from 1 to 8 carbon atoms, R₂ is hydrogen or alkylcarbonyl and each of R₃ and R₄ is hydrogen, chlorine, fluorine or methyl.

9. A compound of claim 1 which is 2-amino-3-(5-imidazolyl)-2-vinylpropionic acid.

10. A compound of claim 1 which is 2-acetylene-2-amino-3-(5-imidazolyl)propionic acid or a pharmaceutically acceptable salt thereof.

* * * * *